United States Patent
Manku et al.

(10) Patent No.: US 10,570,083 B2
(45) Date of Patent: Feb. 25, 2020

(54) COMPOSITIONS COMPRISING OXO-DERIVATIVES OF FATTY ACIDS AND METHODS OF MAKING AND USING SAME

(71) Applicant: DS Biopharma Limited, Dublin (IE)

(72) Inventors: Mehar Manku, Birmingham (GB); John Climax, Dublin (IE); David Coughlan, Dublin (IE)

(73) Assignee: DS Biopharma Limited (IE)

( * ) Notice: Subject to any disclaimer, the term of this patent is extended or adjusted under 35 U.S.C. 154(b) by 154 days.

(21) Appl. No.: 15/921,211

(22) Filed: Mar. 14, 2018

(65) Prior Publication Data

US 2018/0201566 A1 Jul. 19, 2018

Related U.S. Application Data

(62) Division of application No. 15/153,476, filed on May 12, 2016, now Pat. No. 10,047,033.

(60) Provisional application No. 62/160,863, filed on May 13, 2015.

(51) Int. Cl.
| | | |
|---|---|---|
| *A61K 31/202* | (2006.01) | |
| *A61K 31/232* | (2006.01) | |
| *C07C 59/76* | (2006.01) | |
| *A61K 45/06* | (2006.01) | |

(52) U.S. Cl.
CPC ............ *C07C 59/76* (2013.01); *A61K 31/202* (2013.01); *A61K 31/232* (2013.01); *A61K 45/06* (2013.01)

(58) Field of Classification Search
CPC .......................... A61K 31/202; A61K 31/232
See application file for complete search history.

(56) References Cited

U.S. PATENT DOCUMENTS

| 9,889,106 B2 | 2/2018 | Kelliher et al. |
| 2007/0105954 A1 | 5/2007 | Puri |
| 2013/0102575 A1 | 4/2013 | Manku et al. |

FOREIGN PATENT DOCUMENTS

| JP | H04507397 | 12/1992 |
| JP | 2000191525 | 7/2000 |
| JP | 2004528360 | 9/2004 |
| JP | 2005179211 | 7/2005 |
| WO | WO 2010/125340 | 11/2010 |
| WO | WO2014/105576 | 7/2014 |
| WO | WO2014/118097 | 8/2014 |
| WO | WO2014/142364 | 9/2014 |

OTHER PUBLICATIONS

Banno, "Diversified Approach to Acne Care by Using Natural Raw Materials," Fragrance Journal, 35(5):36-41 (May 2007) (with English translation).
Miller et al., Guinea pig epidermis synthesizes 15-hydroxy-8,11,13-eicosatrienoic acid (15OH-20:3n-6) from dihomogammalinolenic acid: a potent lipoxygenase inhibitor derived from dietary primrose oil, Clinical Research 35(3):704A (1989).
Ziboh et al., "Significance of lipoxygenase-derived monohydroxy fatty acids in cutaneous biology," Prostaglandins & other Lipid Mediators 63(1-2):3-13 (Dec. 2000).
Armstrong et al., "Inhibitory and mechanistic investigations of oxo-lipids with human lipoxygenase isozymes," Bioorganic & Medicinal Chemistry. 22(15):4293-4297 (May 21, 2014).
Hirahashi et al., "Immunomodulation with eicosapentaenoic acid supports the treatment of autoimmune small-vessel vasculitis," Scientific Reports. vol. 4 (Sep. 2014).
International Search Report and Written Opinion dated Sep. 5, 2016 for International Application No. PCT/IB16/00732.

*Primary Examiner* — Yong S. Chong
(74) *Attorney, Agent, or Firm* — Perkins Coie LLP

(57) ABSTRACT

The present disclosure provides 15-oxo-EPA and 15-oxo-DGLA, compositions comprising 15-oxo-EPA and/or 15-oxo-DGLA, and methods of treating and/or preventing fibrosis, skin disorders, inflammation, kidney disease or renal dysfunction in a subject in need thereof by administering 15-oxo-EPA and/or 15-oxo-DGLA.

20 Claims, No Drawings

COMPOSITIONS COMPRISING OXO-DERIVATIVES OF FATTY ACIDS AND METHODS OF MAKING AND USING SAME

PRIORITY CLAIM

This application is a divisional application of U.S. patent application Ser. No. 15/153,476, filed May 12, 2016, which claims priority to U.S. Provisional Patent Application Ser. No. 62/160,863, filed May 13, 2015, the entire contents of which is incorporated herein by reference.

FIELD

The present disclosure provides (5Z,8Z,11Z,13E,17Z)-15-oxoicosa-5,8,11,13,17-pentaenoic acid (also referred to as 15-oxo-EPA) and (8Z,11Z,13E)-15-oxoicosa-8,11,13-trienoic acid (also referred to as 15-oxo-DGLA), compositions, formulations and dosage units comprising 15-oxo-EPA or 15-oxo-DGLA, and methods for treating or preventing fibrosis (e.g., liver fibrosis), skin disorders, inflammation, kidney disease or renal dysfunction by administering 15-oxo-EPA or 15-oxo-DGLA (or a pharmaceutical composition comprising same) to a subject in need thereof.

SUMMARY

In some embodiments, the present disclosure provides methods of treating and/or preventing fibrosis (e.g., liver fibrosis), skin disorders, inflammation, kidney disease or renal dysfunction in a subject in need thereof, the method comprising administering to the subject a composition comprising 15-oxo-EPA.

In some embodiments, the present disclosure provides methods of treating fibrosis in a subject on fibrosis therapy, the method comprising administering to the subject a composition comprising 15-oxo-EPA.

In some embodiments, the present disclosure provides compositions for treating and/or preventing fibrosis (e.g., liver fibrosis), skin disorders, inflammation, kidney disease or renal dysfunction in a subject in need thereof, wherein the compositions comprise an effective amount of 15-oxo-EPA.

In some embodiments, the present disclosure provides uses of 15-oxo-EPA (or a pharmaceutical composition comprising 15-oxo-EPA) for treating and/or preventing fibrosis (e.g., liver fibrosis), skin disorders, inflammation, kidney disease or renal dysfunction in a subject.

In some embodiments, the present disclosure provides a pharmaceutical composition comprising 15-oxo-EPA.

In some embodiments, the present disclosure provides methods of treating and/or preventing fibrosis (e.g., liver fibrosis), skin disorders, inflammation, kidney disease or renal dysfunction in a subject in need thereof, the method comprising administering to the subject a composition comprising 15-oxo-DGLA.

In some embodiments, the present disclosure provides methods of treating fibrosis in a subject on fibrosis therapy, the method comprising administering to the subject a composition comprising 15-oxo-DGLA.

In some embodiments, the present disclosure provides compositions for treating and/or preventing fibrosis (e.g., liver fibrosis), skin disorders, inflammation, kidney disease or renal dysfunction in a subject in need thereof, wherein the compositions comprise an effective amount of 15-oxo-DGLA.

In some embodiments, the present disclosure provides uses of 15-oxo-DGLA (or a pharmaceutical composition comprising 15-oxo-DGLA) for treating and/or preventing fibrosis (e.g., liver fibrosis), skin disorders, inflammation, kidney disease or renal dysfunction in a subject.

In some embodiments, the present disclosure provides a pharmaceutical composition comprising 15-oxo-DGLA.

Other features and advantages of the technology disclosed herein will be apparent from the following detailed description.

DETAILED DESCRIPTION

In one embodiment, the present disclosure provides compositions comprising 15-oxo-EPA, 15-oxo-DGLA, or a combination thereof, and methods of using same for treating and/or preventing fibrosis (e.g., liver fibrosis), skin disorders, inflammation, kidney disease or renal dysfunction in a subject in need thereof.

15-oxo-EPA has the general structure and IUPAC name shown in Formula (I):

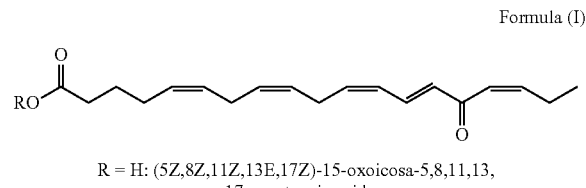

R = H: (5Z,8Z,11Z,13E,17Z)-15-oxoicosa-5,8,11,13, 17-penatenoic acid 15-oxo-EPA can be synthesized from eicosapentaenoic acid (EPA) according to methods known in the art. As used herein, the term "15-oxo-EPA" may refer to 15-oxo-EPA in its free acid form and/or a derivative (R≠H) thereof, such as a pharmaceutically acceptable ester, a conjugate, or a salt (R is an ion) consistent with Formula (I), or mixtures of any of the foregoing. In some embodiments, the 15-oxo-EPA is used in the free acid form (i.e., R=H). Alternatively, pharmaceutically acceptable esters or salts of 15-oxo-EPA are used in certain embodiments of the present disclosure. In some embodiments, the 15-oxo-EPA is in the form of a $C_{1-4}$ alkyl ester such as methyl ester (R=$CH_3$) or ethyl ester (R=$CH_2CH_3$) form.

As used herein, "EPA" refers to eicosa-5,8,11,14,17-pentaenoic acid, also known as 20:5n-3, an omega-3 fatty acid. EPA is readily obtainable through commercial sources.

15-oxo-DGLA has the general structure and IUPAC name shown in Formula (II):

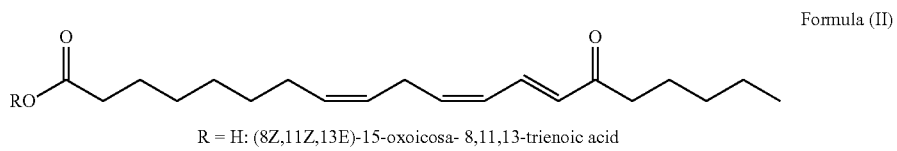

R = H: (8Z,11Z,13E)-15-oxoicosa- 8,11,13-trienoic acid 15-oxo-DGLA can be synthesized from dihomo-gamma-linolenic acid (DGLA) according to methods known in the art. As used herein, the term "15-oxo-DGLA" may refer to 15-oxo-DGLA in its free acid form and/or a derivative (R≠H) thereof, such as a pharmaceutically acceptable ester, a conjugate, or a salt (R is an ion) consistent with Formula (I), or mixtures of any of the foregoing. In some embodiments, the 15-oxo-DGLA is used in the free acid form (i.e., R═H). Alternatively, pharmaceutically acceptable esters or salts of 15-oxo-DGLA are used in certain embodiments of the present disclosure. In some embodiments, the 15-oxo-DGLA is in the form of a $C_{1-4}$ alkyl ester such as methyl ester (R═CH$_3$) or ethyl ester (R═CH$_2$CH$_3$) form.

As used herein, "DGLA" refers to eicosa-8,11,14-trienoic acid, also known as 20:3n-6, an omega-6 fatty acid. DGLA is readily obtainable through commercial sources.

Accordingly, in one aspect of the present disclosure, a method of treating and/or preventing fibrosis in a subject is provided, comprising administering to the subject a therapeutically effective amount of 15-oxo-EPA or a composition comprising 15-oxo-EPA.

In another aspect of the present disclosure, a method of treating and/or preventing fibrosis in a subject is provided, comprising administering to the subject a therapeutically effective amount of 15-oxo-DGLA or a composition comprising 15-oxo-DGLA.

The present disclosure provides 15-oxo-EPA, or a composition comprising 15-oxo-EPA, for use in the treatment and/or prevention of fibrosis (e.g., liver fibrosis), skin disorders, inflammation, kidney disease or renal dysfunction.

The present disclosure also provides 15-oxo-DGLA, or a composition comprising 15-oxo-DGLA, for use in the treatment and/or prevention of fibrosis (e.g., liver fibrosis), skin disorders, inflammation, kidney disease or renal dysfunction.

The present disclosure provides a use of 15-oxo-EPA, or a composition comprising 15-oxo-EPA, in the manufacture of a medicament for treating and/or preventing fibrosis (e.g., liver fibrosis), skin disorders, inflammation, kidney disease or renal dysfunction.

The present disclosure provides a use of 15-oxo-DGLA, or a composition comprising 15-oxo-DGLA, in the manufacture of a medicament for treating and/or preventing fibrosis (e.g., liver fibrosis), skin disorders, inflammation, kidney disease or renal dysfunction.

In another aspect, the present disclosure provides a pharmaceutical composition comprising a therapeutically effective amount of 15-oxo-EPA. The 15-oxo-EPA may be the sole active ingredient (e.g., API) in the pharmaceutical composition and in the methods and uses as stated herein. The 15-oxo-EPA may be the sole active ingredient. Alternatively, the 15-oxo-EPA may be combined for co-formulation or co-administration with another agent or agents for treating and/or preventing fibrosis. If an additional active agent or agents is/are to be used, the 15-oxo-EPA can be co-formulated as a single dosage unit, or the 15-oxo-EPA and the additional fibrosis therapeutic agent can be formulated as two to a plurality of dosage units for coordinated, combination or concomitant administration.

In another aspect, the present disclosure provides a pharmaceutical composition comprising a therapeutically effective amount of 15-oxo-DGLA. The 15-oxo-DGLA may be the sole active ingredient (e.g., API) in the pharmaceutical composition and in the methods and uses as stated herein. The 15-oxo-DGLA may be the sole active ingredient. Alternatively, the 15-oxo-DGLA may be combined for co-formulation or co-administration with another agent or agents for treating and/or preventing fibrosis. If an additional active agent or agents is/are to be used, the 15-oxo-DGLA can be co-formulated as a single dosage unit, or the 15-oxo-DGLA and the additional fibrosis therapeutic agent can be formulated as two to a plurality of dosage units for coordinated, combination or concomitant administration.

The present disclosure also provides formulations of 15-oxo-EPA and formulations comprising 15-oxo-EPA and methods of using these formulations for treating and/or preventing fibrosis (e.g., liver fibrosis), skin disorders, inflammation, kidney disease or renal dysfunction.

The present disclosure also provides formulations of 15-oxo-DGLA and formulations comprising 15-oxo-DGLA and methods of using these formulations for treating and/or preventing fibrosis (e.g., liver fibrosis), skin disorders, inflammation, kidney disease or renal dysfunction.

The present disclosure further provides a pharmaceutical composition for oral delivery, comprising 15-oxo-EPA. That composition may comprise a pharmaceutically acceptable excipient. The 15-oxo-EPA may be in any form as discussed herein. The 15-oxo-EPA may be present in one or more divided dosage units in amounts from about 1 mg to about 10,000 mg.

The present disclosure further provides a pharmaceutical composition for oral delivery, comprising 15-oxo-DGLA. That composition may comprise a pharmaceutically acceptable excipient. The 15-oxo-DGLA may be in any form as discussed herein. The 15-oxo-DGLA may be present in one or more divided dosage units in amounts from about 1 mg to about 10,000 mg.

15-oxo-EPA

In one embodiment, compositions of the present disclosure comprise 15-oxo-EPA as an active ingredient. As used herein, the term "15-oxo-EPA" refers to 15-oxo-EPA in its free acid form and/or a pharmaceutically acceptable ester, conjugate or salt thereof, or mixtures of any of the foregoing. 15-oxo-EPA can be synthesized via ways known in the art. In one embodiment, 15-oxo-EPA can be synthesized from EPA in a 2-step process as shown in Scheme 1:

Scheme 1.

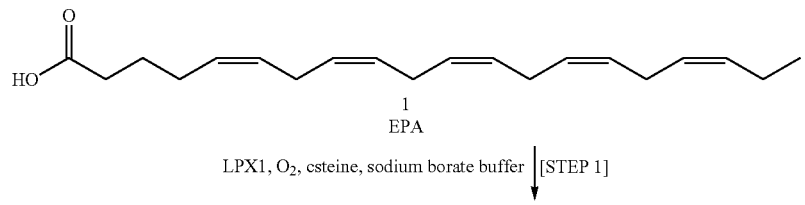

1
EPA

LPX1, O$_2$, csteine, sodium borate buffer ↓ [STEP 1]

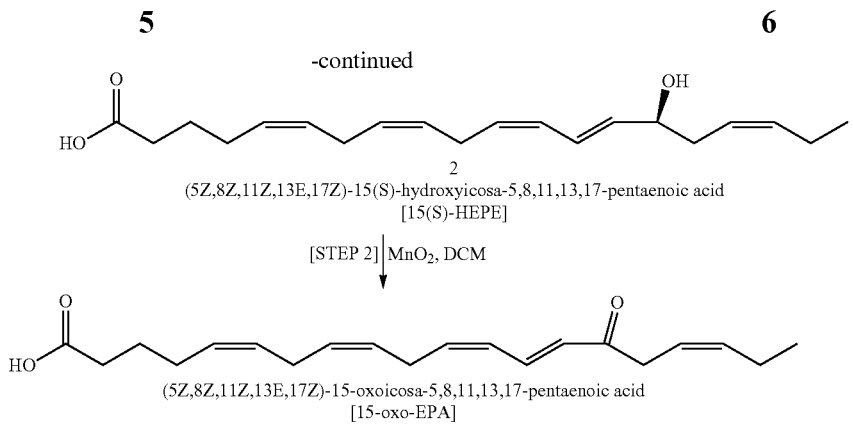

2
(5Z,8Z,11Z,13E,17Z)-15-(S)-hydroxyicosa-5,8,11,13,17-pentaenoic acid
[15(S)-HEPE]

[STEP 2] MnO$_2$, DCM (5Z,8Z,11Z,13E,17Z)-15-oxoicosa-5,8,11,13,17-pentaenoic acid
[15-oxo-EPA]

In Step 1, EPA (1) is converted to its corresponding 15(S)-hydroxy compound (Compound 2) (15-(S)-HEPE) using reagents oxygen, borax, L-cysteine and specific enzyme LPX1 of appropriate concentration. In Step 2, the 15-(S)-HEPE (Compound 2) obtained from Step 1 undergoes oxidation with MnO$_2$ in dichloromethane (DCM) to obtain 15-oxo-EPA.

A derivative of 15-oxo-EPA may be used instead, though the term "derivative of 15-oxo-EPA" does not include any derivative compound missing the oxo group of 15-oxo-EPA. The term "pharmaceutically acceptable" in the present context means that the substance in question does not produce unacceptable toxicity to the subject or interaction with other components of the composition.

In one embodiment, the 15-oxo-EPA is in the form of an ester, such as an ethyl ester (also referred to herein as E-15-oxo-EPA or ethyl-15-oxo-EPA). In some embodiments, the 15-oxo-EPA comprises a $C_1$-$C_5$ alkyl ester of 15-oxo-EPA. In another embodiment, the 15-oxo-EPA comprises 15-oxo-EPA methyl ester, 15-oxo-EPA propyl ester, or 15-oxo-EPA butyl ester.

In another embodiment, the 15-oxo-EPA comprises lithium 15-oxo-EPA, mono, di- or triglyceride 15-oxo-EPA or any other ester or salt of 15-oxo-EPA, or the free acid form of 15-oxo-EPA.

In various embodiments, the present disclosure provides pharmaceutical compositions, for example orally deliverable compositions, comprising 15-oxo-EPA. In one embodiment, the compositions comprise a therapeutically effective amount of 15-oxo-EPA. In one embodiment, the pharmaceutical composition comprises about 0.1% to about 99%, about 1% to about 95%, about 5% to about 90% by weight of 15-oxo-EPA.

In one embodiment, the pharmaceutical composition comprises about at least about 70%, at least about 80% or at least about 90%, by weight, of 15-oxo-EPA. In one embodiment, the pharmaceutical composition comprises at least about 50%, at least about 60%, at least about 70%, at least about 80% or at least about 90%, by weight of 15-oxo-EPA.

In another embodiment, 15-oxo-EPA is present in a composition of the present disclosure in an amount of about 1 mg to about 10,000 mg, 25 mg to about 7500 mg, about 25 mg to about 5000 mg, about 50 mg to about 5000 mg, about 50 mg to about 3000 mg, about 75 mg to about 2500 mg, or about 100 mg to about 1000 mg, for example about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In one embodiment, 15-oxo-EPA present in a composition of the present disclosure comprises at least 90% by weight 15-oxo-EPA. 15-oxo-EPA compositions can comprise even higher purity 15-oxo-EPA, for example at least 95% by weight 15-oxo-EPA or at least 97% by weight 15-oxo-EPA, wherein the 15-oxo-EPA is any form of 15-oxo-EPA as set forth herein. The purity of 15-oxo-EPA can further be defined (e.g. impurity profile) by any of the descriptions of 15-oxo-EPA provided herein.

Above are discussed the amounts of the 15-oxo-EPA in the pharmaceutical composition and their purity. The nature of the essential fatty acids and their synthesis is such that the 15-oxo-EPA composition may include moieties from other essential fatty acids in the essential fatty acid metabolic cascade.

In one embodiment, a composition of the present disclosure contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of other omega-3 fatty acids including alpha linolenic acid, stearidonic acid, docosahexaenoic acid (DHA) or derivatives thereof. In other embodiments there is substantially no, or no such other omega-3 fatty acids present.

In another embodiment, 15-oxo-EPA represents at least about 60%, at least about 70%, at least about 80%, at least about 90%, at least about 95%, at least about 97%, at least about 98%, at least about 99%, or 100%, by weight, of all fatty acids present in a composition of the present disclosure.

There may be present some residual eicosapentaenoic acid from the synthesis of the 15-oxo-EPA. There may be not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight EPA. Alternatively, there is substantially no, or no, EPA in a form which has not been modified to the oxo-form.

15-oxo-DGLA

In one embodiment, compositions of the present disclosure comprise 15-oxo-DGLA as an active ingredient. As used herein, the term "15-oxo-DGLA" refers to 15-oxo-DGLA in its free acid form and/or a pharmaceutically acceptable ester, conjugate or salt thereof, or mixtures of any of the foregoing. 15-oxo-DGLA can be synthesized via ways known in the art. In one embodiment, 15-oxo-DGLA can be synthesized from DGLA in a 2-step process as shown in Scheme 2:

Scheme 2.

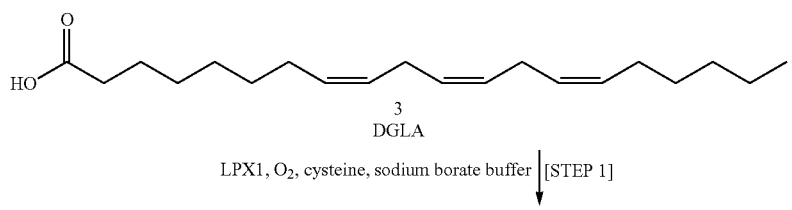

3
DGLA

LPX1, O₂, cysteine, sodium borate buffer ↓ [STEP 1]

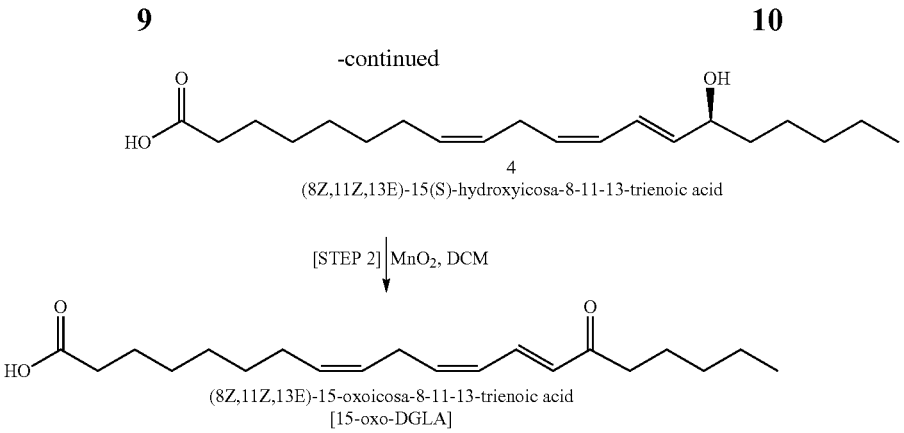

(8Z,11Z,13E)-15(S)-hydroxyicosa-8-11-13-trienoic acid

[STEP 2] MnO₂, DCM (8Z,11Z,13E)-15-oxoicosa-8-11-13-trienoic acid
[15-oxo-DGLA]

In Step 1, DGLA (Compound 3) is converted to its corresponding 15(S)-hydroxy compound (Compound 4) using reagents oxygen, borax, L-cysteine and specific enzyme LPX1 of appropriate concentration. In Step 2, Compound 4 obtained from Step 1 undergoes oxidation with MnO₂ in dichloromethane (DCM) to obtain 15-oxo-DGLA.

A derivative of 15-oxo-DGLA may be used instead, though the term "derivative of 15-oxo-DGLA" does not include any derivative compound missing the oxo group of 15-oxo-DGLA. The term "pharmaceutically acceptable" in the present context means that the substance in question does not produce unacceptable toxicity to the subject or interaction with other components of the composition.

In one embodiment, the 15-oxo-DGLA is in the form of an ester, such as an ethyl ester (also referred to herein as E-15-oxo-DGLA or ethyl-15-oxo-DGLA). In some embodiments, the 15-oxo-DGLA comprises a $C_1$-$C_5$ alkyl ester of 15-oxo-DGLA. In another embodiment, the 15-oxo-DGLA comprises 15-oxo-DGLA methyl ester, 15-oxo-DGLA propyl ester, or 15-oxo-DGLA butyl ester.

In another embodiment, the 15-oxo-DGLA comprises lithium 15-oxo-DGLA, mono, di- or triglyceride 15-oxo-DGLA or any other ester or salt of 15-oxo-DGLA, or the free acid form of 15-oxo-DGLA.

In various embodiments, the present disclosure provides pharmaceutical compositions, for example orally deliverable compositions, comprising 15-oxo-DGLA. In one embodiment, the compositions comprise a therapeutically effective amount of 15-oxo-DGLA. In one embodiment, the pharmaceutical composition comprises about 0.1% to about 99%, about 1% to about 95%, about 5% to about 90% by weight of 15-oxo-DGLA.

In one embodiment, the pharmaceutical composition comprises about at least about 70%, at least about 80% or at least about 90%, by weight, of 15-oxo-DGLA. In one embodiment, the pharmaceutical composition comprises at least about 50%, at least about 60%, at least about 70%, at least about 80% or at least about 90%, by weight of 15-oxo-DGLA.

In another embodiment, 15-oxo-DGLA is present in a composition of the present disclosure in an amount of about 1 mg to about 10,000 mg, 25 mg to about 7500 mg, about 25 mg to about 5000 mg, about 50 mg to about 5000 mg, about 50 mg to about 3000 mg, about 75 mg to about 2500 mg, or about 100 mg to about 1000 mg, for example about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In one embodiment, 15-oxo-DGLA present in a composition of the present disclosure comprises at least 90% by weight 15-oxo-DGLA. 15-oxo-DGLA compositions can comprise even higher purity 15-oxo-DGLA, for example at least 95% by weight 15-oxo-DGLA or at least 97% by weight 15-oxo-DGLA, wherein the 15-oxo-DGLA is any form of 15-oxo-DGLA as set forth herein. The purity of 15-oxo-DGLA can further be defined (e.g. impurity profile) by any of the descriptions of 15-oxo-DGLA provided herein.

Above are discussed the amounts of the 15-oxo-DGLA in the pharmaceutical composition and their purity. The nature of the essential fatty acids and their synthesis is such that the 15-oxo-DGLA composition may include moieties from other essential fatty acids in the essential fatty acid metabolic cascade.

In one embodiment, a composition of the present disclosure contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of other omega-3 fatty acids including alpha linolenic acid, stearidonic acid, docosahexaenoic acid (DHA) or derivatives thereof. In other embodiments there is substantially no, or no such other omega-3 fatty acids present.

In another embodiment, 15-oxo-DGLA represents at least about 60%, at least about 70%, at least about 80%, at least about 90%, at least about 95%, at least about 97%, at least about 98%, at least about 99%, or 100%, by weight, of all fatty acids present in a composition of the present disclosure.

There may be present some residual DGLA from the synthesis of the 15-oxo-DGLA. There may be not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight DGLA. Alternatively, there is substantially no, or no, DGLA in a form which has not been modified to the oxo-form.

Additional Active Agents

In one embodiment, the pharmaceutical composition further comprises at least one or more additional active agent(s). In one embodiment, the pharmaceutical composition comprises an amount of the additional active agent that is less than the generally recognized therapeutically effective amount for that agent. In one embodiment, the pharmaceutical composition comprises an amount of the additional active agent that is equal to or greater than the generally recognized therapeutically effective amount for that agent.

In some embodiments, the additional active agent is a hepatitis C virus (HCV) non-antiviral agent, an HCV antiviral agent, a hepatitis B virus (HBV) non-antiviral agent, an HBV antiviral agent, a primary biliary cirrhosis agent, an alcoholic hepatitis agent, a primary sclerosing cholangitis agent, a non-alcoholic steatohepatitis (NASH) agent, an autoimmune hepatitis agent, a pulmonary fibrosis agent, a cystic fibrosis agent, a renal fibrosis agent, a skin fibrosis agent, a myelofibrosis agent, an eosinophilic esophagitis agent, an anti-TGF-β agent, an anti-CTGF agent, a recombinant human serum amyloid P agent, an anti-IL-4 agent, an anti-IL-5 agent (e.g., mepolizumab), an anti-IL-13 agent, a neurochemical receptor agent, an anti-IL-17A agent, a Hh or Hh(R) SMO antagonist, a CCR5 antagonist, a CCR4 cell recruitment inhibitor, a CXCR4 antagonist, an anti-CXCR4 agent, a CXCR3 antagonist, an anti-CCL17 agent, a NOX inhibitor, copaxone, adiponectin, an AMPK agonist, Y-box binding protein-1, a myofibroblast recruitment inhibitor, an anti-Th17 MMP inducer, an anti-extracellular matrix deposition compound, an adenosine receptor antagonist, a microRNA (miR) agent, a stem cell, tenofovir, an anti-collagen crosslinking agent (e.g., simtuzumab, mogamulizumab), or an angiotensin II receptor blocker (ARB) selected from the group consisting of: valsartan, telmisartan, losartan, irbesartan, azilsartan, eprosartan, olmesartan, or a combination of any of the foregoing.

In one embodiment, the one or more additional active agent(s) comprises, consists essentially of, or consists of telmisartan.

In one embodiment, the present disclosure provides a composition (e.g., a pharmaceutical composition) comprising 15-oxo-EPA and telmisartan as the only active agents.

In one embodiment, the present disclosure provides a composition (e.g., a pharmaceutical composition) comprising 15-oxo-DGLA and telmisartan as the only active agents.

In one embodiment, 15-oxo-EPA and one or more active agent(s) are present in a composition of the present disclosure, or are co-administered in a weight ratio of 15-oxo-EPA:additional agent of about 1:1000 to about 1000:1, about 1:500 to about 500:1, about 1:100 to about 100:1, about 1:50 to about 50:1, about 1:25 to about 25:1, about 1:10 to about 10:1, about 1:5 to about 5:1, about 1:4 to about 4:1 about 1:3 to about 3:1, about 1:2 to about 2:1 or about 1:1.

In one embodiment, 15-oxo-DGLA and one or more active agent(s) are present in a composition of the present disclosure, or are co-administered in a weight ratio of 15-oxo-DGLA:additional agent of about 1:1000 to about 1000:1, about 1:500 to about 500:1, about 1:100 to about 100:1, about 1:50 to about 50:1, about 1:25 to about 25:1, about 1:10 to about 10:1, about 1:5 to about 5:1, about 1:4 to about 4:1 about 1:3 to about 3:1, about 1:2 to about 2:1 or about 1:1.

Dosage Forms

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In some embodiments, compositions of the present disclosure are in the form of orally deliverable dosage forms or units. Non-limiting examples of suitable dosage forms include tablets (e.g. suspension tablets, bite suspension tablets, rapid dispersion tablets, chewable tablets, etc), caplets, capsules (e.g. a soft or a hard gelatin capsule or HPMC capsule), lozenges, sachets, cachets, troches, pellets, suspension, elixirs, syrups or any other solid dosage form reasonably adapted for oral administration. The terms "oral delivery" and "oral administration" herein include any form of delivery wherein the agent or composition is placed in the mouth of the subject under treatment, whether swallowed or not. This therefore includes buccal and sublingual administration, as well as esophagael administration.

Alternatively, compositions of the present disclosure can also be formulated for rectal, topical, or parenteral (e.g. subcutaneous, intramuscular, intravenous and intradermal or infusion) delivery.

In discussing the amount of 15-oxo-EPA or 15-oxo-DGLA in a composition of the present disclosure, this may be split over several dosage forms. There is a limit as to the size for oral administration. For example, if a subject is to be administered 1 to 4 g 15-oxo-EPA or 1 to 4 g 15-oxo-DGLA per day, this may be by up to 4 capsules, each providing 1 g 15-oxo-EPA or 15-oxo-DGLA, or up to 8 capsules each providing 500 mg 15-oxo-EPA or 15-oxo-DGLA.

Compositions of the present disclosure can be in the form of liquid dosage forms or dose units to be imbibed directly or they can be mixed with food or beverage prior to ingestion. Non-limiting examples of suitable liquid dosage forms include solutions, suspensions, elixirs, syrups, liquid aerosol formulations, and the like.

In another embodiment, compositions of the present disclosure comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition. By way of example only, a pharmaceutical composition according to the present disclosure may comprise one or more of: antioxidants, surfactants, preservatives, flavouring agents, co-solvents, viscosity aids, suspension aids, and lipophilic phases.

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, niacinamide, butylated hydroxyltoluene (BHT), butylated hydroxylanisol (BHA), and the like. In one embodiment, the pharmaceutical composition comprises about 0.01 wt. % to about 2 wt. % of an antioxidant, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

Therapeutic Methods

The compositions and formulations disclosed herein may be used in the treatment of fibrosis, inflammation and inflammatory disorders, kidney diseases and renal dysfunction. In one embodiment the fibrosis is associated with an organ or tissue associated with a lung, a liver, a heart, a kidney, one or more eyes, mediastinum, bone marrow, retroperitoneaum, skin, an intestine, a joint, a reproductive organ, or a combination thereof. In some embodiments, the fibrosis is associated with liver tissue.

In some embodiments, the fibrosis is associated with non-alcoholic fatty liver disease (NAFLD). In some embodiments, an NAFLD activity score (NAS) is reduced in the subject after administration of the composition. In some embodiments, the NAS is reduced in the subject compared to baseline. In some embodiments, the NAS is reduced in comparison to a second subject who has not been administered the composition. In some embodiments, the second subject has been administered a placebo. In some embodiments, the second subject is on fibrosis therapy.

In some embodiments, the subject is on fibrosis therapy. In some embodiments, the fibrosis therapy is continued during administration of the composition. In other embodiments, the fibrosis therapy is discontinued during administration of the composition. For example, in some embodiments the subject is on telmisartan therapy and, after commencing a therapeutic method comprising administration of a composition comprising 15-oxo-EPA or 15-oxo-DGLA as disclosed herein, the telmisartan therapy is discontinued.

In some embodiments, the inflammatory disease is selected from acne vulgaris, asthma, autoimmune diseases, autoinflammatory diseases, celiac disease, chronic prostatitis, glomerulonephritis, inflammatory bowel disease, pelvic inflammatory disease, reperfusion injury, rheumatoid arthritis, sarcoidosis, transplant rejection, vasculitis, and interstitial cystitis, among others.

In some embodiments, the composition is orally administered. In some embodiments, the 15-oxo-EPA or the 15-oxo-DGLA is the only active ingredient in the composition. In other embodiments, the composition further comprises an additional agent for affecting the therapy. In some embodiments, the additional agent is telmisartan.

In some embodiments, the present disclosure provides a method of treating fibrosis in a subject on fibrosis therapy, the method comprising administering to the subject a composition comprising 15-oxo-EPA. In some embodiments, the fibrosis is associated with an organ or tissue selected from the group consisting of: lung, liver, heart, kidney, eye, mediastinum, bone marrow, retroperitoneaum, skin, intestine, joint, a reproductive organ, and a combination thereof. In some embodiments, the fibrosis is liver fibrosis. In some embodiments, the fibrosis is associated with non-alcoholic fatty liver disease (NAFLD). In some embodiments, an NAFLD activity score (NAS) is reduced in the subject after administration of the composition. In some embodiments, the NAS is reduced in the subject compared to baseline. In some embodiments, the NAS is reduced in comparison to a second subject who has not been administered the composition. In some embodiments, the second subject has been administered a placebo. In some embodiments, the second subject is on fibrosis therapy. In some embodiments, the fibrosis therapy comprises administration of an HCV non-antiviral agent, an HCV antiviral agent, an HBV non-antiviral agent, an HBV antiviral agent, a primary biliary cirrhosis agent, an alcoholic hepatitis agent, a primary sclerosing cholangitis agent, a NASH agent, an autoimmune hepatitis agent, a pulmonary fibrosis agent, a cystic fibrosis agent, a renal fibrosis agent, a skin fibrosis agent, a myelofibrosis agent, an eosinophilic esophagitis agent, an anti-TGF-β agent, an anti-CTGF agent, a recombinant human serum amyloid P agent, an anti-IL-4 agent, an anti-IL-5 agent (e.g., mepolizumab), an anti-IL-13 agent, a neurochemical receptor agent, an anti-IL-17A agent, a Hh or Hh(R) SMO antagonist, a CCR5 antagonist, a CCR4 cell recruitment inhibitor, a CXCR4 antagonist, an anti-CXCR4 agent, a CXCR3 antagonist, an anti-CCL17 agent, a NOX inhibitor, copaxone, adiponectin, an AMPK agonist, Y-box binding protein-1, a myofibroblast recruitment inhibitor, an anti-Th17 MMP inducer, an anti-extracellular matrix deposition compound, an adenosine receptor antagonist, a microRNA (miR) agent, a stem cell, tenofovir, an anti-collagen crosslinking agent (e.g., simtuzumab, mogamulizumab), or an angiotensin II receptor blocker (ARB) selected from the group consisting of: valsartan, telmisartan, losartan, irbesartan, azilsartan, eprosartan, olmesartan, or a combination of any of the foregoing. In some embodiments, the subject is on fibrosis therapy. In some embodiments, the fibrosis therapy is continued during administration of the composition. In some embodiments, the second subject is on fibrosis therapy. In some embodiments, the composition is orally administered.

In some embodiments, the method further comprises identifying the subject as having fibrosis before administering the composition comprising 15-oxo-EPA. In some embodiments, the method further comprises identifying the subject as having an increased risk of developing fibrosis before administering the composition comprising 15-oxo-EPA. In some embodiments, the step of identifying comprises determining a NAS associated with the subject. In some embodiments, the NAS associated with the subject is at least 3. In some embodiments, the step of identifying comprises screening for a genetic mutation in a nucleic acid molecule associated with the subject. In some embodiments, the step of identifying comprises obtaining an analysis of blood and/or serum associated with the subject. In some embodiments, the step of identifying comprises examining a tissue associated with the subject. In some embodiments, the step of examining comprises analyzing a histological tissue sample (e.g., a biopsy) associated with the subject.

In some embodiments, the present disclosure provides a method of treating fibrosis in a subject on fibrosis therapy, the method comprising administering to the subject a composition comprising 15-oxo-DGLA. In some embodiments, the fibrosis is associated with an organ or tissue selected from the group consisting of: lung, liver, heart, kidney, eye, mediastinum, bone marrow, retroperitoneaum, skin, intestine, joint, a reproductive organ, and a combination thereof. In some embodiments, the fibrosis is liver fibrosis. In some embodiments, the fibrosis is associated with non-alcoholic fatty liver disease (NAFLD). In some embodiments, an NAFLD activity score (NAS) is reduced in the subject after administration of the composition. In some embodiments, the NAS is reduced in the subject compared to baseline. In some embodiments, the NAS is reduced in comparison to a second subject who has not been administered the composition. In some embodiments, the second subject has been administered a placebo. In some embodiments, the second subject is on fibrosis therapy. In some embodiments, the fibrosis therapy comprises administration of an HCV non-antiviral agent, an HCV antiviral agent, an HBV non-antiviral agent, an HBV antiviral agent, a primary biliary cirrhosis agent, an alcoholic hepatitis agent, a primary sclerosing cholangitis agent, a NASH agent, an autoimmune hepatitis agent, a pulmonary fibrosis agent, a cystic fibrosis agent, a renal fibrosis agent, a skin fibrosis agent, a myelofibrosis agent, an eosinophilic esophagitis agent, an anti-TGF-β agent, an anti-CTGF agent, a recombinant human serum amyloid P agent, an anti-IL-4 agent, an anti-IL-5 agent (e.g., mepolizumab), an anti-IL-13 agent, a neurochemical receptor agent, an anti-IL-17A agent, a Hh or Hh(R) SMO antagonist, a CCR5 antagonist, a CCR4 cell recruitment inhibitor, a CXCR4 antagonist, an anti-CXCR4 agent, a CXCR3 antagonist, an anti-CCL17 agent, a NOX inhibitor, copaxone, adiponectin, an AMPK agonist, Y-box binding protein-1, a myofibroblast recruitment inhibitor, an anti-Th17 MMP inducer, an anti-extracellular matrix deposition compound, an adenosine receptor antagonist, a microRNA (miR) agent, a stem cell, tenofovir, an anti-collagen crosslinking agent (e.g., simtuzumab, mogamulizumab), or an angiotensin II receptor blocker (ARB) selected from the group consisting of: valsartan, telmisartan, losartan, irbesartan, azilsartan, eprosartan, olmesartan, or a combination of any of the foregoing. In some embodiments, the subject is on fibrosis therapy. In some embodiments, the fibrosis therapy is continued during administration of the composition. In some embodiments, the second subject is on fibrosis therapy. In some embodiments, the composition is orally administered.

In some embodiments, the method further comprises identifying the subject as having fibrosis before administering the composition comprising 15-oxo-DGLA. In some embodiments, the method further comprises identifying the subject as having an increased risk of developing fibrosis before administering the composition comprising 15-oxo-DGLA. In some embodiments, the step of identifying comprises determining a NAS associated with the subject. In some embodiments, the NAS associated with the subject is at least 3. In some embodiments, the step of identifying comprises screening for a genetic mutation in a nucleic acid molecule associated with the subject. In some embodiments, the step of identifying comprises obtaining an analysis of blood and/or serum associated with the subject. In some embodiments, the step of identifying comprises examining a tissue associated with the subject. In some embodiments, the step of examining comprises analyzing a histological tissue sample (e.g., a biopsy) associated with the subject.

In some embodiments, methods of the present disclosure cause a NAS value to decrease in a subject. In some embodiments, the method further comprises determining a second, lower NAS value associated with the subject after administering the composition for a period of time.

In one embodiment, the present disclosure provides a method of treating a skin disease or disorder in a subject in need thereof, the method comprising orally administering to the subject a pharmaceutical composition comprising 15-oxo-EPA. Non-limiting examples of skin disorders and diseases include acne, atopic dermatitis, psoriasis, pruritus/itch, radiation protection, dry skin, anti-aging, and photoprotection.

In one embodiment, the present disclosure provides a method of treating a skin disease or disorder in a subject in need thereof, the method comprising orally administering to the subject a pharmaceutical composition comprising 15-oxo-DGLA. Non-limiting examples of skin disorders and diseases include acne, atopic dermatitis, psoriasis, pruritus/itch, radiation protection, dry skin, anti-aging, and photoprotection.

The term "acne" herein refers to any disease or disorder of the skin that presents with one or more acneiform eruptions such as papules, pustules, cysts, and the like. Non-limiting examples of acne include acne vulgaris, acne necrotica, halogen acne, chloracne, occupational acne, oil acne, tar acne, acne *aestivalis*, tropical acne, acne cosmetica, pomade acne, acne keloidalis nuchae, acne mechanica, excoriated acne, acne medicamentosa, infantile acne, neonatal acne, acne conglobata, acne fulminans, acne miliaris necrotica, miliaris disseminatus faciei, and, and other skin disorders associated with acneiform eruptions.

In one embodiment, the present disclosure provides a method of treating or preventing acne associated with *P. acnes* in a subject in need thereof. In one embodiment, the method comprises administering to the subject a composition as disclosed herein.

In one embodiment, the present disclosure provides a method of inhibiting *P. acnes* including, for example, its growth, colonization and/or infection in a subject in need thereof. In one embodiment, the method comprises contacting *P. acnes* with a composition as disclosed herein.

In one embodiment, the method further comprises washing an affected area of the skin (and/or to an area of the skin that is generally prone to development of acneiform eruptions) prior to administering the composition. As used herein, the term "washing" refers generally to any method known to those of skill in the art for cleansing the skin, exfoliating the skin, removing dirt, oil, dead skin cells and the like from the skin, etc.

In one embodiment, the present disclosure provides a method of treating hypertension (e.g., pulmonary hypertension) in a subject in need thereof, the method comprising orally administering to the subject a pharmaceutical composition comprising 15-oxo-EPA as disclosed herein.

In one embodiment, the present disclosure provides a method of treating hypertension (e.g., pulmonary hypertension) in a subject in need thereof, the method comprising orally administering to the subject a pharmaceutical composition comprising 15-oxo-DGLA as disclosed herein.

In one embodiment, the method comprises administering a pharmaceutical composition as disclosed herein to a subject once per day, twice per day, three times per day, or more than three times per day.

Unless otherwise defined, all technical and scientific terms used herein have the same meaning as commonly understood by one of ordinary skill in the art to which this present disclosure pertains. Although methods and materials similar or equivalent to those described herein can be used in the practice of the present disclosure, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

While the present disclosure is capable of being embodied in various forms, the present description below of several embodiments is made with the understanding that the present disclosure is to be considered as an exemplification of the present disclosure, and is not intended to limit the technology disclosed herein to the specific embodiments illustrated. Headings are provided for convenience only and are not to be construed to limit the technology disclosed herein in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

As used herein, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

What is claimed is:

1. (5Z,8Z,11Z,13E,17Z)-15-oxoicosa-5,8,11,13,17-pentaenoic acid.

2. A composition comprising (5Z,8Z,11Z,13E,17Z)-15-oxoicosa-5,8,11,13,17-pentaenoic acid.

3. (8Z,11Z,13E)-15-oxoicosa-8,11,13-trienoic acid.

4. A composition comprising (8Z,11Z,13E)-15-oxoicosa-8,11,13-trienoic acid.

5. The composition of claim 2, wherein the composition is a pharmaceutical composition comprising about 0.1 g to about 4 g of (5Z,8Z,11Z,13E,17Z)-15-oxoicosa-5,8,11,13,17-pentaenoic acid.

6. The composition of claim 2, wherein the (5Z,8Z,11Z,13E,17Z)-15-oxoicosa-5,8,11,13,17-pentaenoic acid is in a free acid form, an esterified form, or an ethyl ester form.

7. The composition of claim 5, wherein the composition is formulated for treating liver fibrosis.

8. The composition of claim 7, wherein the liver fibrosis is non-alcoholic fatty liver disease (NAFLD).

9. The composition of claim 5, wherein (5Z,8Z,11Z,13E,17Z)-15-oxoicosa-5,8,11,13,17-pentaenoic acid is the only active ingredient in the pharmaceutical composition.

10. The composition of claim 5, wherein the pharmaceutical composition is formulated for oral administration.

11. The composition of claim 4, wherein the composition is a pharmaceutical composition comprising about 0.1 g to about 4 g of (8Z,11Z,13E)-15-oxoicosa-8,11,13-trienoic acid.

12. The composition of claim 4, wherein the (8Z,11Z,13E)-15-oxoicosa-8,11,13-trienoic acid is in a free acid form, an esterified form, or an ethyl ester form.

13. The composition of claim 12, wherein the pharmaceutical composition is formulated for treating liver fibrosis.

14. The composition of claim 13, wherein the liver fibrosis is non-alcoholic fatty liver disease (NAFLD).

15. The composition of claim 11, wherein the (8Z,11Z,13E)-15-oxoicosa-8,11,13-trienoic acid is the only active ingredient in the pharmaceutical composition.

16. The composition of claim 11, wherein the pharmaceutical composition is formulated for oral administration.

17. A composition comprising (5Z,8Z,11Z,13E,17Z)-15-oxoicosa-5,8,11,13,17-pentaenoic acid and (8Z,11Z,13E)-15-oxoicosa-8,11,13-trienoic acid.

18. The composition of claim 17, wherein the composition is a pharmaceutical composition.

19. The composition of claim 18, wherein either the (5Z,8Z,11Z,13E,17Z)-15-oxoicosa-5,8,11,13,17-pentaenoic acid or the (8Z,11Z,13E)-15-oxoicosa-8,11,13-trienoic acid is in a free acid form, an esterified form, or an ethyl ester form.

20. The composition of claim 19, wherein the composition is formulated for treating liver fibrosis.

* * * * *